United States Patent [19]

Legrow et al.

[11] Patent Number: 5,384,383
[45] Date of Patent: Jan. 24, 1995

[54] PRISTINE PHENYLPROPYLALKYLSILOXANES

[75] Inventors: Gary E. Legrow, Midland; Joan E. Sudbury-Holtschlag, Saginaw, both of Mich.

[73] Assignee: Dow Corning Corporation, Midland, Mich.

[21] Appl. No.: 189,531

[22] Filed: Jan. 31, 1994

[51] Int. Cl.$^6$ .............................................. C08G 77/06
[52] U.S. Cl. ...................................... 528/23; 528/43; 556/453; 556/460; 556/461; 556/462
[58] Field of Search .................... 528/43, 23; 556/453, 556/460, 461, 462

[56] References Cited

U.S. PATENT DOCUMENTS

| | | | |
|---|---|---|---|
| 3,088,964 | 5/1963 | Ryan | 260/448.2 |
| 3,186,964 | 6/1965 | Kookootsedes | 260/46.5 |
| 3,221,040 | 11/1965 | Pater | 260/448.2 |
| 3,839,384 | 10/1974 | Morehouse | 260/448.2 |

FOREIGN PATENT DOCUMENTS

| | | | |
|---|---|---|---|
| 5735198 | 5/1974 | Japan | C07F 7/08 |
| 446933 | 6/1990 | Japan | C08G 77/38 |

OTHER PUBLICATIONS

Ryan, J. W. and Speier, J. L., "Addition of Silicon Hydrides to Olefinic Double Bonds. IV, The Addition to Styrene and x-Methylstyrene", Jul. 9, 1959, pp. 2052–2053.

Primary Examiner—Melvyn I. Marquis
Attorney, Agent, or Firm—Sharon K. Severance

[57] ABSTRACT

This invention pertains to pristine phenylpropylalkylsiloxanes consisting of mixtures of linear and cyclic siloxanes containing the structure

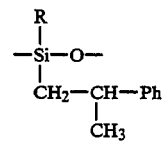

and a method for their preparation. The pristine phenylpropylalkylsiloxanes of the instant invention contain no detectable silicon hydride (—SiH), free organics (—C≡C—) or free inorganics. Additionally, the pristine phenylpropylalkylsiloxanes of the instant invention are high refractive index organosilicone polymers.

15 Claims, No Drawings

PRISTINE PHENYLPROPYLALKYLSILOXANES

BACKGROUND OF THE INVENTION

This invention pertains to pristine phenylpropylalkylsiloxanes and a method for their preparation. The pristine phenylpropylalkylsiloxanes of the instant invention contain no detectable silicon hydride (—SiH), free organics (—C≡—) or free inorganics. Additionally, the pristine phenylpropylalkylsiloxanes of the instant invention are high refractive index organosilicone polymers.

Silicone polymers which have high refractive indices, dimethylsilicone-like sensory properties, organic compatibility and high tolerance to strong acid media are desired in the art. Dimethylsilicone fluids typically have refractive indices of approximately 1.4 regardless of the structure or molecular weight of the fluid. Although some alkylmethylsilicones have improved organic compatibility as well as dimethylsilicone-like sensory properties, they generally do not have refractive indices greater than about 1.45. Further, the alkylmethylsilicones that have a refractive index that high are generally waxes. Phenyl containing silicones can provide the desired refractive index since the refractive index can be correlated to the amount of phenyl substitution relative to methyl substitution. However, phenyl-containing polymers where the phenyl is directly bonded to the silicone have a low tolerance to acid media and are costly to produce. This limits the applications in which these phenyl-containing polymer can be used. It has been found that pristine phenylpropylalkylsiloxanes of the instant invention can provide the desired properties.

When 2-phenylpropylalkylsiloxanes are produced by the standard hydrosilylation route wherein α-methylstyrene is reacted with a —SiH containing organopolysiloxane several difficulties are encountered which prohibit the production of low cost, pristine phenylpropylalkylsiloxanes. The first problem is that when the reaction is run with a slight excess of alphamethylstyrene and less than 150 ppm platinum the reaction does not go to completion resulting in phenylpropylalkylsiloxanes that contain silicon hydride (—SiH). At higher concentrations of platinum the reaction goes to completion (no detectable —SiH) but the resulting product has an undesirable color and odor. Further, use of higher amounts of platinum make the product costly to produce.

Disclosed in "Addition of Silicon Hydrides to Olefinic Double Bonds. IV. The Addition to Styrene and α-Methylstyrene" by J. Speier and J. Ryan, Journal of Organic Chemistry, 24, 2052(1959), is a method for making phenylpropylalkyl hydrolysates as an intermediate in the production of phenylpropylalkyl cyclosiloxanes. The method disclosed in Speier and Ryan consists of producing distilled phenylpropylmethyldichlorosilane. The distilled phenylpropylmethyldichlorosilane is then hydrolyzed and the cyclosiloxanes are recovered by distillation. Speier and Ryan does not disclose a process for producing pristine phenylpropylalkylsiloxanes.

U.S. Pat. No. 3,088,964 to Ryan discloses several methods for producing phenylpropylmethylsiloxanes. The first method comprises hydrolyzing phenylpropylmethyldichlorosilane. The hydrolyzate is then cracked with a basic catalyst to produce phenylpropylmethylcyclosiloxanes. Another method comprises reacting α-methylstyrene with an organosiloxane containing —SiH atoms. Neither of the methods disclosed in U.S. Pat. No. 3,088,964 are capable of producing pristine phenylpropylalkylsiloxanes.

U.S. Pat. No. 3,186,944 to Kookootsedes and Speier discloses the use of 2-phenylpropylmethylsiloxane, ethylmethylsiloxane or propylmethylsiloxane copolymers as mold release agents. These copolymers may be prepared by hydrosilylation of α-methylstyrene with an excess of methylhydrogen siloxane followed by hydrosilylation with an excess of propylene or ethylene. Another method comprises hydrosilylation of α-methylstyrene with methylhydrogen siloxane and thereafter copolymerizing with ethylmethylsiloxane or propylmethylsiloxane. A third method comprises cohydrolyzing phenylpropyl and ethyl or propyl methyldichlorosilanes. None of these methods are capable of producing pristine phenylpropylalkylsiloxanes.

U.S. Pat. No. 3,221,040 to Pater discloses several methods for making copolymeric organosilicon lubricants. Pater discloses that the lubricants can be produced by (1) equilibration of cyclosiloxanes, hexahydrocarbyldisiloxane and tetra(phenylethyl)tetramethylcyclotetrasiloxane in an acidic or basic medium or (2) cohydrolysis and co-condensation of the corresponding chlorosilanes. Pater does not disclose methods for making pristine phenylpropylalkylsiloxanes.

Finally, U.S. Pat. No. 3,839,384 to Morehouse discloses a high resilience polyether urethane foam which contains a minor amount of an aralkyl modified siloxane. The aralkyl modified siloxanes can be produced by the method disclosed in U.S. Pat. No. 3,221,040 discussed above. Morehouse does not disclose pristine phenylpropylalkylsiloxanes or methods for making the same.

It is an object of the instant invention to provide pristine phenylpropylalkylsiloxanes which contain no detectable silicon hydride (—SiH), free organics (—C≡—) or free inorganics and are colorless and odorless.

It is further an object of the instant invention to provide a method for the preparation of the pristine phenylpropylalkylsiloxanes which allows for the production of pristine phenylpropylalkylsiloxanes having varying refractive indices.

SUMMARY OF THE INVENTION

The instant invention pertains to pristine phenylpropylalkylsiloxanes comprised of phenylpropylalkylsiloxanes selected from the group consisting of: (I) a mixture consisting essentially of

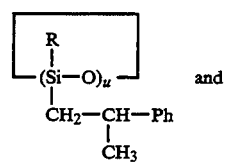

and

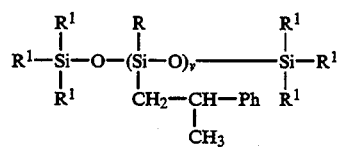

and (II) a mixture consisting essentially of

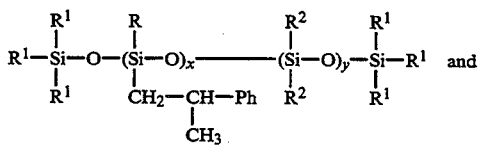

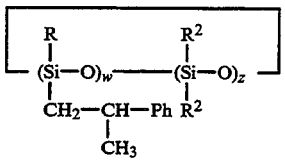

wherein Ph represents a phenyl group, each R is independently an alkyl group having 1 to 4 carbon atoms; each $R^1$ is independently an alkyl radical having 1 to 6 carbon atoms or 2-phenylpropyl; each $R^2$ is independently selected from the group consisting of monovalent hydrocarbon groups having from 1 to 14 carbon atoms and monovalent substituted hydrocarbon groups having from 1 to 10 carbon atoms; u has a value of 3 to 6; v has a value of 1 to 50; x has a value of 1 to 50, y has a value of 1 to with the proviso that $x+y=2$ to 100; w has a value of 1 to 5, and z has a value of 1 to 5, with the further proviso that $w+z=3$ to 6;

wherein the pristine phenylpropylalkylsiloxanes contain no detectable silicon hydride (—SiH), free organics (—C≡—), or free inorganics, and is odorless and colorless.

The method for producing the pristine phenylpropylalkylsiloxanes of the instant invention comprises hydrolyzing pure phenylpropylalkyldichlorosilane followed by acid catalyzed equilibration in the presence of a triorganosilyl endblocker and optionally a diorganocyclicsiloxane.

THE INVENTION

The instant invention pertains to pristine phenylpropylalkylsiloxanes wherein the pristine phenylpropylalkylsiloxanes contain no detectable silicon hydride (—SiH), free organics (—C≡—), and free inorganics, and are odorless and colorless. The pristine phenylpropylalkylsiloxanes may be linear and/or cyclic siloxanes selected from phenylpropylalkylsiloxanes containing the structure

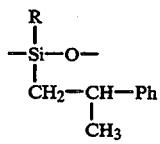

wherein Ph represents a phenyl group, each R is independently an alkyl group having 1 to 4 carbon atoms.

The pristine phenylpropylalkylsiloxanes may be exemplified by phenylpropylalkylsiloxanes selected from the group consisting of phenylpropylalkylsiloxanes having the formulae:

(I) a mixture consisting essentially of

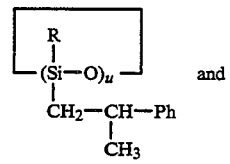

and

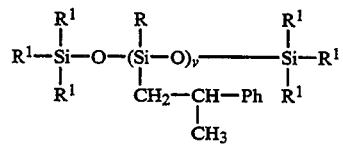

and (II) a mixture consisting essentially of

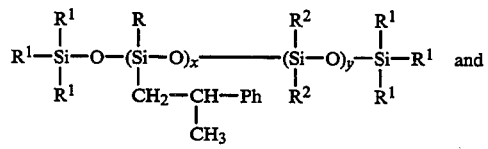

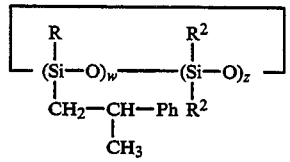

wherein Ph represents a phenyl group, each R is independently an alkyl group having 1 to 4 carbon atoms; each $R^1$ is independently an alkyl radical having 1 to 6 carbon atoms or 2-phenylpropyl; each $R^2$ is independently selected from the group consisting of monovalent hydrocarbon groups having from 1 to 14 carbon atoms and monovalent substituted hydrocarbon groups having from 1 to 10 carbon atoms; u has a value of 3 to 6; v has a value of 1 to 50; x has a value of 1 to 50, y has a value of 1 to 99, with the proviso that $x+y=2$ to 100; w has a value of 1 to 5, and z has a value of 1 to 5, with the further proviso that $w+z=3$ to 6.

In the preceding formulas each R is independently an alkyl group having from 1 to 4 carbon atoms. R may be exemplified by methyl, ethyl, propyl, iso-propyl and butyl. It is preferred that each of the R groups be methyl.

$R^1$ is independently selected from the group consisting of an alkyl radical having 1 to 6 carbon atoms or 2-phenylpropyl. $R^1$ can be, for example methyl, ethyl, propyl, and others. It is preferred that each $R^1$ be methyl.

$R^2$ is independently selected from the group consisting of monovalent hydrocarbon groups having from 1 to 14 carbon atoms and monovalent substituted hydrocarbon groups having from 1 to 10 carbon atoms. $R^2$ can be, for example methyl, ethyl, propyl, and others. It is preferred that each $R^2$ be methyl.

Further, in the preceding formulas, u has a value of 3 to 6, preferably 3 and 4; v has a value of 1 to 50, preferably 1 to 10; x has a value of 1 to 50, preferably 1 to 10; y has a value of 1 to 99; preferably 1 to 20 with the proviso that $x+y=2$ to 100; w has a value of 1 to 5, and z has a value of 1 to 5 with the further proviso that $v+w=3$ to 6, preferably 3 to 4.

The pristine phenylpropylalkylsiloxanes of the instant invention may be characterized as consisting of no detectable silicon hydride (—SiH), free organics (—C≡—), or free inorganics, and they are odorless and colorless. No detectable silicon hydride means silicon hydride of less than 1 ppm as determined by manometric reduction with sodium butylate analysis. This analytical method comprises reacting a sample of the phenylpropylalkyl siloxane with a saturated solution of sodium butylate in a closed system. The reaction produces hydrogen gas when there is —SiH present which is then measured manometrically.

No detectable free organics means unsaturation of less than 1 ppm as determined by iodine monochloride reduction analysis. This analytical method, based on ASTM D 460 and ASTM D 1959, comprises reacting vinyl or other unsaturated structures in organic materials with iodine monochloride. Potassium iodide is mixed with a sample of the phenylpropylalkylsiloxanes. The excess reagent is then determined by titration of the liberated $I_2$ with sodium thiosulfate.

No detectable free inorganics means free inorganics of less than 1 ppm as determined by atomic absorption analysis. This analytical method comprises acid digestion under oxidizing conditions to convert the metallic elements to the ionic state. Any $SiO_2$ is removed by treatment with HF. The water-soluble metallic elements are quantitatively determined by atomic absorption spectroscopy. Sample solutions are aspirated through a flame and the absorbance determined. Standard curves are used to relate the absorbance to concentration.

The color of the phenylpropylalkylsiloxane is determined by APHA technique. This analytical method, based on ASTM 1209, comprises visual measurement of the color in essentially waterwhite liquids. The sample is compared with a series of numbered standards. The number reported is the number of the standard that is the best match. Colorless indicates a color of 0 on the APHA scale.

Other analytical methods known in the art which are capable of measurement in the ppm range can be used to determine if the phenylpropylalkylsiloxanes contain no detectable silicon hydride, organics and inorganics. Further, other analytical methods known in the art which are capable of determining color in the phenylpropylalkylsiloxane can be used in the instant invention to determine if the phenylpropylalkylsiloxanes are colorless. Odor can be determined by smelling the samples or other known analytical techniques.

The pristine phenylpropylalkylsiloxanes of the instant invention are prepared by a method comprising hydrolyzing pure phenylpropylalkyldichlorosilane followed by acid catalyzed equilibration in the presence of a triorganosilyl endblocker and optionally a diorganocyclicsiloxane.

In the method for the preparation of the pristine phenylpropylalkylsiloxanes, pure phenylpropylalkyldichlorosilane is hydrolyzed by known hydrolysis procedures. By pure phenylpropylalkyldichlorosilane it is meant a phenylpropylalkyldichlorosilane having a purity of greater than 99.9%, preferably greater than 99.99% and containing no detectable silicon hydride, free organics, or free inorganics. The phenylpropylalkyldichlorosilanes may be produced by any method known in the art, for example hydrosilylation of α-methylstyrene and methyl hydrogen dichlorosilane, and stripped or optionally distilled to achieve the required purity. It is preferred to produce the phenylpropylalkyldichlorosilane, by hydrosilylation of α-methylstyrene in the presence of a dry heterogeneous catalyst, under anhydrous conditions.

The phenylpropylalkyldichlorosilanes are hydrolyzed by contacting the phenylpropylalkyldichlorosilane with water. The amount of water present should be at least a stoichiometric (2 moles of water per mole of dichlorosilane) amount. Preferably there should be at least 5 to 100 moles of water per mole of dichlorosilane, more preferably 10 to 50. The excess water allows for the separation and removal of the hydrogen chloride by-product produced during the reaction.

The hydrolysis reaction is carried out at a temperature of 0° C. to 100° C., preferably 50° C. to 100° C., at atmospheric pressure. The hydrolysis reaction may be carried out at sub or supra atmospheric conditions allowing for reaction temperatures outside of this range.

The reaction times will vary according to equipment and the amount being produced however, completion of the reaction can be easily ascertained by known analytical techniques. Typically a time of 2 to 8 hours is sufficient when the reaction is carried out as a batch process.

It is preferred to carry out the hydrolysis in the presence of a solvent. The solvent should be one that is a non-reactive hydrocarbon liquid. Suitable solvents include, but are not limited to, benzene, toluene, xylene, heptane and others. Toluene is the preferred solvent.

Following the hydrolysis reaction the product layer and water layer are separated. The product layer may then be washed with additional quantities of water until the water being separated has a near neutral or neutral pH. The product layer comprising the hydrolysis reaction product and solvent is distilled by methods known in the art to remove any additional water and the solvent.

The hydrolysis of the phenylpropylalkyldichlorosilanes results in a hydrolysis reaction product consisting of a mixture

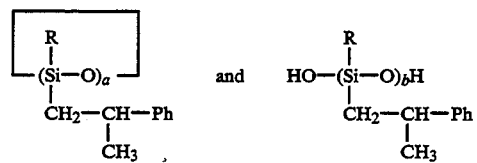

wherein each R is as described above, a has a value of 3 to 6 and b has a value of 1 to 10. The ratio of cyclics to linears in the hydrolysis reaction product may vary from 1:4 to 4:1 depending on the amount of solvent used, the acid concentration in the aqueous phase and the reaction temperature. For example, increasing the amount of solvent, acid concentration in the aqueous phase and/or reaction temperature all produce increased amounts of the cyclic phenylpropylalkylsiloxanes.

Following hydrolysis, the hydrolysis reaction product is equilibrated using a heterogeneous acid catalyst in the presence of a triorganosilyl endblocker and optionally a diorganocyclicsiloxane. Triorganosilyl endblockers useful in the instant invention are triorganosilyl endblockers that contain a radical of the formula $R^1_3Si$— wherein each $R^1$ is independently an alkyl radical having 1 to 6 carbon atoms or 2-phenylpropyl. $R^1$ can be, for example methyl, ethyl, propyl, and others. The source of the triorganosilyl endblocker radicals can be any material which under reaction conditions forms the triorganosilyl radical of the formula $R^1_3Si-$. By adding a triorganosilyl endblocker the polymer length of the product polydiorganosiloxane can be controlled.

Examples of triorganosilyl endblockers useful in the instant invention include, but are not limited to, hexamethyldisiloxane, trimethyl endblocked linear polydimethylsiloxanes, and others. The preferred triorganosilyl endblocker is hexamethyldisiloxane.

The amount of triorganosilyl endblocker useful herein is dependent on the desired polymer chain length and can be determined by one skilled in the art. It is preferred to use from about 0.1 to 75 weight percent of the reaction mixture. It is further preferred that the triorganosilyl endblocker be present in a concentration of 0.1 to 50 weight percent of the reaction mixture. The reaction mixture, as used herein, refers to the amount of all silicone reactants.

When the hydrolysis reaction product is equilibrated with only a triorganosilyl endblocker the resulting product is a mixture consisting of

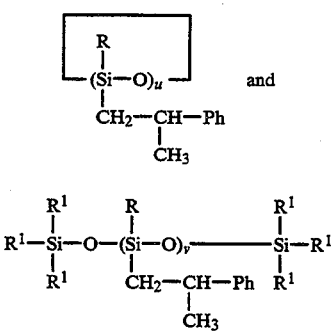

wherein Ph represents phenyl and R, $R^1$, u and v are as described above.

Diorganocyclicsiloxanes useful in the instant invention are diorganocyclicsiloxanes that are capable of polymerizing with the hydrolysis reaction product in the presence of an acid catalyst. The diorganocyclicsiloxanes useful in the instant invention are of the formula

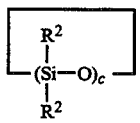

wherein each $R^2$ is independently selected from the group consisting of monovalent hydrocarbon groups having from 1 to 14 carbon atoms and monovalent substituted hydrocarbon groups having from 1 to 10 carbon atoms; and c has a value of 3 to 6. Examples of useful diorganocyclicsiloxanes include, but are not limited to, dimethylcyclosiloxanes, propylmethylcyclosiloxanes and others.

The amount of diorganocycticsiloxane useful in the instant invention is from 0.1 to 75 weight percent of the reaction mixture, preferably from 10 to 60 weight percent. The use of higher amounts of diorganocyclicsiloxane will produce phenylpropylalkylsiloxanes that have lower refractive indices.

When the hydrolysis reaction product is equilibrated with a triorganosilyl endblocker and diorganocyclicsiloxanes the resulting product is a mixture consisting of

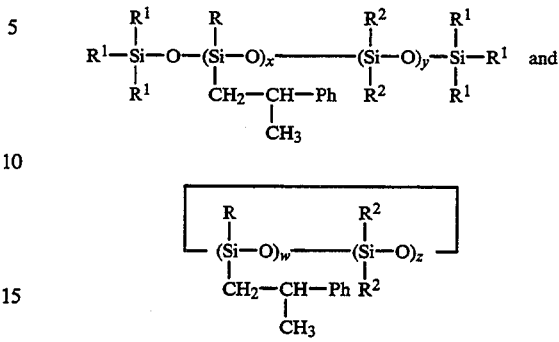

wherein Ph represents phenyl and each R, $R^1$, $R^2$, and x, y, w and z are as described above.

The equilibration reaction is carried out in the presence of a heterogeneous acid catalyst. Catalysts useful in the instant invention may be exemplified by, but not limited to, acid clays such as Tonsil Optimum FF Course produced by Sud Chemie; and acid ion exchange resins such as Dowex ® DR-2040 produced by Dow Chemical Company, Midland, MI, and Amberlyst ® 15 produced by Rohm and Hass Co.; and others.

The equilibration reaction is carried out at a temperature of from room temperature to 130° C., preferably from 50° C. to 110° C. at atmospheric pressure. Pressures above or below atmospheric may be employed thus allowing temperatures outside of this range. The reaction times will vary according to equipment and batch size. The reaction time will vary according to equipment and the amount of product being produced and can be easily ascertained by known analytical methods. Typically in a batch reaction a time of 1 hour is sufficient for completion. When the reaction is carried out in a continuous or semi-continuous manner the time for completion is typically 3 to 5 minutes of contact.

The equilibration reaction may be run on a continuous, semicontinuous, or batch reactor. A continuous reactor comprises a means wherein the reactants are introduced and products are withdrawn simultaneously. The continuous reactor may be a tank, a tubular structure, a tower, or some other like structure, the overall design not being essential. The preferred continuous reactor is a fixed bed reactor. A semi-continuous reactor comprises a means wherein some of the reactants are charged at the beginning and the remaining are fed continuously as the reaction progresses. The product may optionally be simultaneously withdrawn from the semi-continuous reactor. A batch reactor comprises a means wherein all the reactants are added at the beginning and processing is carried out according to a predetermined course of reaction during which no reactant is fed into or removed from the reactor. Typically a batch reactor will be a tank with or without agitation means.

The pristine phenylpropylalkylsiloxanes are useful as hydraulic fluids and lubricating oils. They are also useful in cosmetic formulations.

So that those skilled in the art can understand and appreciate the invention taught herein, the following examples are presented, it being understood that these examples should not be used to limit the scope of this invention found in the claims attached hereto.

EXAMPLE 1

Preparation of 2-phenylpropylmethyldichlorosilane

To a stirred suspension of 1 gram of dry 5% Platinum on carbon in 500 grams of MeHSiCl$_2$ at 40° C. was added 500 grams of alpha-methylstyrene over a period of 1 hour. The rate of addition was used to control the exotherm. After complete addition, the product was filtered under a nitrogen atmosphere (to prevent hydrolysis) and the product was distilled at reduced pressure yielding 968 grams (98% theory) of 2-phenylpropylmethy dichlorosilane, bp: 131/40mm, n25/D=1.5085, d25/4=1.11.

EXAMPLE 2

Synthesis of 2-phenylpropylmethylsiloxane hydrolysate

A solution of 466 grams of the 2-phenylpropylmethyl dichlorosilane prepared in Example 1 in 356 grams of toluene was rapidly added with stirring to a flask containing 822 grams of distilled water. An exotherm was observed during the addition to about 60° C. After complete addition, the mixture was heated to 100° C. and stirred for an additional 2 hours to ensure complete hydrolysis, and then cooled to room temperature. The lower aqueous acid layer was separated, and the upper siloxane in toluene layer was washed followed by separation, 4 times with 500 ml aliquots of distilled water. The final separation provided a water layer that was very near neutral in pH. The remaining organic layer was slightly hazy and heated to azeotropically remove water with a Dean Stark trap. Less than 1 ml of water was removed leaving a clear, colorless solution. The solution was then heated to 100° C. and stripped at reduced pressure to remove the toluene, leaving 342 grams (96% of theory) of clear, colorless and odorless 2-phenylpropylmethylsiloxane hydrolysate, n25/D=1.529 and viscosity=350 cp. Analysis of this product formula (PhCHMeCH$_2$MeSiO)$_3$, 20 wt % cyclotetrasiloxane of the by Si$^{29}$ NMR identified it to be 10% cyclotrisiloxane of the formula (PhCHMeCH$_2$MeSiO)$_4$, and 70 wt % OH terminated linear siloxanes of the average formula HO(PhCHMeCH$_2$MeSiO)$_y$H where y has an average value of 6.

EXAMPLE 3

Preparation of trimethyl endblocked phenylpropylmethylpolysiloxane

A solution of 22.67 grams of the phenylpropylmethylsiloxane hydrolysate prepared in Example 2 and 17.37 grams of hexamethyldisiloxane, containing 0.40 grams of Dowex ® DR-2040 resin was heated and stirred at 100° C. for 7 hours. After cooling to room temperature the mixture was filtered to remove the Dowex ® resin and the clear product was stripped at 110° C. under reduced pressure to remove volatiles leaving a clear, colorless product with n25/D=1.4811 and a viscosity of 16 cSt. Odor was removed from this product by filtration through carbon black. Si$^{29}$ NMR analysis of this product identified it as consisting of 6 wt % (PhCHMeCH$_2$MeSiO)$_4$, and 94 wt % Me$_3$SiO(PhCHMeCH$_2$MeSiO)$_{2.5}$SiMe$_3$.

EXAMPLE 4

Preparation of trimethyl endblocked phenylpropylmethylpolysiloxane

A solution of 22.7 grams of the phenylpropylmethylsiloxane hydrolysate prepared in Example 2 and 17.4 grams of hexamethyldisiloxane, containing 0.41 grams of Dowex ® DR-2040 resin was heated and stirred at 80° C. for 6 hours. After cooling to room temperature the mixture was filtered to remove the Dowex ® resin and the clear product was stripped at 110° C. under reduced pressure to remove volatiles leaving a clear, colorless product with n25/D=1.4966 and a viscosity of 47 cSt. Si$^{29}$ NMR analysis of this product identified it as consisting of 10 wt % (PhCHMeCH$_2$MeSiO)$_4$, and 90 wt % Me$_3$SiO(PhCHMeCH$_2$MeSiO)$_{3.4}$SiMe$_3$.

EXAMPLE 5

Preparation of trimethyl endblocked phenylpropylmethylpolysiloxane

A solution of 38.3 grams of the phenylpropylmethylsiloxane hydrolysate prepared in Example 2 and 1.8 grams of hexamethyldisiloxane containing 0.40 grams of Dowex ® DR-2040 resin was heated and stirred at 80° C. for 7 hours. After cooling to room temperature the mixture was filtered to remove the Dowex ® resin and the clear product was stripped at 110° C. under reduced pressure to remove volatiles leaving a clear, colorless product with n25/D=1.5214 and a viscosity of 212 cSt. Si$^{29}$ NMR analysis of this product identified it as consisting of 5.8 wt % (PhCHMeCH$_2$MeSiO)$_3$, 36.2 wt % (PhCHMeCH$_2$MeSiO)$_4$, and 58 wt % Me$_3$SiO(PhCHMeCH$_2$MeSiO)$_{7.1}$SiMe$_3$.

EXAMPLE 6

Preparation of a trimethyl endblocked dimethyl, phenylpropylmethylpolysiloxane.

A solution of 19.5 grams of the 2-phenylpropylmethylsiloxane hydrolysate prepared in Example 2, 16.2 grams of octamethylcyclotetrasiloxane containing 4 wt % decamethylcyclopentasiloxane and 4.8 grams of hexamethyldisiloxane containing 0.43 grams of Dowex ® DR-2040 resin was heated and stirred at 80° C. for 6 hours. After cooling to room temperature the mixture was filtered to remove the Dowex ® resin and the clear product was stripped at 90° C. under reduced pressure to remove volatiles leaving a clear, colorless and odorless product with n25/D=1.4765 and a viscosity of 40 cSt. Si$^{29}$ NMR analysis of this product identified it as consisting of 4 wt % (PhCHMeCH$_2$MeSiO) 3, 32 wt % (PhCHMeCH$_2$MeSiO)$_4$, 0.8 wt % of (Me$_2$SiO)$_4$ and 64 wt % Me$_3$SiO(MeSiO)$_{3.7}$(PhCHMeCH$_2$MeSiO)$_{2.9}$SiMe$_3$.

EXAMPLE 7

Preparation of a trimethyl endblocked dimethyl, phenylpropylmethylpolysiloxane.

A solution of 76.3 grams of 2-phenylpropylmethylsiloxane hydrolysate comprising 42 wt % cyclosiloxanes and 58 wt % —OH endblocked linears having an average dp of 6.2; 31.8 grams of octamethylcyclotetrasiloxane containing approx. 4 wt % decamethylcyclopentasiloxane; and 17.7 grams of hexamethyldisiloxane, containing 2.54 grams of Dowex ® DR-2040 resin was heated and stirred at 80° C. for 6 hours. After cooling to room temperature the mixture was filtered to remove the Dowex ® resin and the clear product was stripped at 90° C. under reduced pressure to remove volatiles leaving a clear, colorless and odorless product with n25/D=1.4813 and a viscosity of 48 cSt. Si$^{29}$ NMR analysis of this product identified it as consisting of 25 wt % (PhCHMeCH$_2$MeSiO)$_4$, 3 wt % of (Me$_2$Si- O)$_4$ and 72 wt % Me$_3$SiO(MeSiO)$_{4.0}$(PhCHMeCH$_2$MeSiO)$_{4.5}$SiMe$_3$.

COMPARATIVE EXAMPLE 1

Preparation of a trimethyl endblocked dimethyl, phenylpropylmethylpolysiloxane.

A dispersion of 25.8 grams (0.104 equivalents SiH) of a dimethyl methylhydrogenpolysiloxane and 0.016 grams of a dried carbon supported platinum catalyst (5 wt % Pt) were heated and stirred. When the pot temperature reached 70° C., 14.2 grams (0.120 equivalents) of alpha-methylstyrene (99%) was added in a dropwise manner to the pot. The reaction mixture was heated to 120° C. and stirred for an additional 20 hours. The SiH content after a reaction time of 4 hours was 773 ppm and after 20 hours was 732 ppm. The product was filtered to remove the carbon supported Pt catalyst. The product was clear and colorless, but possessed a strong odor of α-methylstyrene.

What is claimed is:

1. Pristine phenylpropylalkylsiloxanes selected from the group consisting of:

(I) a mixture consisting essentially of

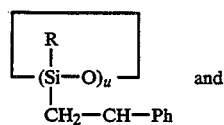

and

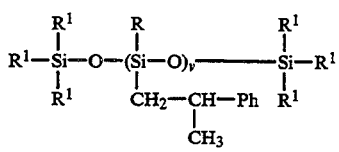

and (II) a mixture consisting essentially of

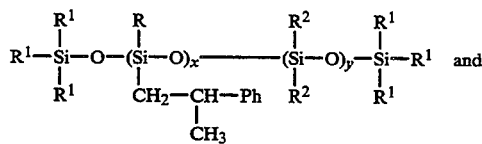

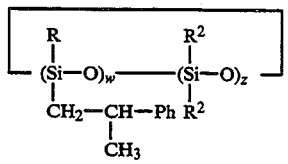

wherein Ph represents a phenyl group, each R is independently an alkyl group having 1 to 4 carbon atoms; each R$^1$ is independently an alkyl radical having 1 to 6 carbon atoms; each R$^2$ is independently selected from the group consisting of monovalent hydrocarbon groups having from 1 to 14 carbon atoms and monovalent substituted hydrocarbon groups having from 1 to 10 carbon atoms; u has a value of 3 to 6; v has a value of 1 to 50; x has a value of 1 to 50, y has a value of 1 to 99, with the proviso that x+y=2 to 100; w has a value of 1 to 5, and z has a value of 1 to 5, with the further proviso that w+z=3 to 6;

wherein the pristine phenylpropylalkylsiloxanes detectable silicon hydride (—SiH), free organics (—C≡—), and free inorganics, and is odorless and colorless.

2. Pristine phenylpropylalkylsiloxanes as claimed in claim 1 wherein each R is methyl.

3. Pristine phenylpropylalkylsiloxanes as claimed in claim 1 wherein each R$^1$ is methyl.

4. Pristine phenylpropylalkylsiloxanes as claimed in claim 1 wherein each R$^2$ is methyl.

5. Pristine phenylpropylalkylsiloxanes as claimed in claim 1 wherein v has a value of 1 to 10.

6. Pristine phenylpropylalkylsiloxanes as claimed in claim wherein x has a value of 1 to 10.

7. Pristine phenylpropylalkylsiloxanes as claimed in claim wherein y has a value of 1 to 20.

8. Pristine phenylpropylalkylsiloxanes consisting essentially of a mixture of phenylpropylalkylsiloxanes having the formula

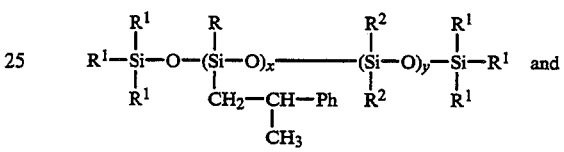

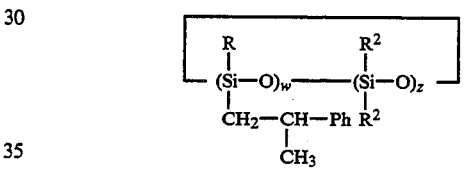

wherein Ph represents a phenyl group, each R is independently an alkyl group having 1 to 4 carbon atoms; each R$^1$ is independently selected from the group consisting of an alkyl radical having 1 to 6 carbon atoms and 2-phenylpropyl; each R$^2$ is independently selected from the group consisting of monovalent hydrocarbon groups having from 1 to 14 carbon atoms and monovalent substituted hydrocarbon groups having from 1 to 10 carbon atoms; x has a value of 1 to 50, y has a value of 1 to 99, with proviso that x+y=2 to 100; w has a value of 1 to 5, and z has a value of 1 to 5, with the proviso that w+z=3 to 6;

wherein the pristine phenylpropylalkylsiloxanes contain no detectable silicon hydride (—SiH), free organics (—C≡—), and free inorganics, and is odorless and colorless.

9. The pristine phenylpropylalkylsiloxanes as claimed in claim 8 wherein R, R$^1$ and R$^2$ are all methyl.

10. Pristine phenylpropylalkylsiloxanes consisting essentially of a mixture of phenylpropylalkylsiloxanes having the formula

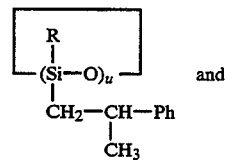

and

-continued

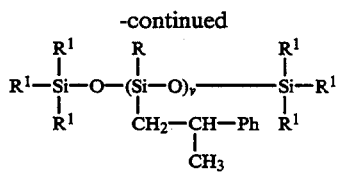

wherein Ph represents a phenyl group, each R is independently an alkyl group having 1 to 4 carbon atoms; each $R^1$ is independently selected from a group consisting of an alkyl radical having 1 to 6 carbon atoms and 2-phenylpropyl; u has a value of 3 to 6; and v has a value of 1 to 50;

wherein the pristine phenylpropylalkylsiloxanes contain no detectable silicon hydride (—SiH), free organics (—C═—), and free inorganics, and is odorless and colorless.

11. The pristine phenylpropylalkylsiloxanes as claimed in claim 10 wherein R, $R^1$ and $R^2$ are all methyl.

12. A method for the production of phenylpropylalkylsiloxanes comprising the steps of
i) hydrolyzing a pure phenylpropylalkyldichlorosilane having a purity of greater than 99.9% and containing no detectable silicon hydride, free organics, or free inorganics and thereafter recovering the hydrolysis reaction product; and
ii) equilibrating the hydrolysis reaction product with a triorganosilyl endblocker in the presence of a heterogeneous acid catalyst.

13. A method for the production of phenylpropylalkylsiloxanes as claimed in claim 12 wherein during the equilibration there is additionally present diorganocyclosiloxanes.

14. A method for the production of phenylpropylalkylsiloxanes as claimed in claim 12 wherein the heterogeneous acid catalyst is an acid ion exchange resin.

15. Pristine phenylpropylalkylsiloxanes produced by a method comprising:
i) hydrolyzing a pure phenylpropylalkyldichlorosilane having a purity of greater than 99.9% and containing no detectable silicon hydride, free organics, or free inorganics and thereafter recovering the hydrolysis reaction product; and
ii) equilibrating the hydrolysis reaction product with a triorganosilyl endblocker in the presence of a heterogeneous acid catalyst.

* * * * *